(12) United States Patent
De Groot et al.

(10) Patent No.: US 11,844,593 B2
(45) Date of Patent: Dec. 19, 2023

(54) SYSTEM AND METHOD FOR NON-INVASIVE DETERMINATION OF BLOOD PRESSURE DIP BASED ON TRAINED PREDICTION MODELS

(71) Applicant: KONINKLIJKE PHILIPS N.V., Eindhoven (NL)

(72) Inventors: Koen Theo Johan De Groot, Sevenum (NL); Mustafa Ghassan Radha, Steensel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 851 days.

(21) Appl. No.: 16/369,790

(22) Filed: Mar. 29, 2019

(65) Prior Publication Data

US 2019/0298195 A1  Oct. 3, 2019

Related U.S. Application Data

(60) Provisional application No. 62/650,488, filed on Mar. 30, 2018.

(51) Int. Cl.
*A61B 5/0225* (2006.01)
*A61B 5/024* (2006.01)
(Continued)

(52) U.S. Cl.
CPC ...... *A61B 5/02255* (2013.01); *A61B 5/02108* (2013.01); *A61B 5/02405* (2013.01);
(Continued)

(58) Field of Classification Search
CPC ............ A61B 2562/18; A61B 5/02255; A61B 5/02405; A61B 5/02416; A61B 5/681; A61B 5/0295; A61B 5/4809
See application file for complete search history.

(56) References Cited

U.S. PATENT DOCUMENTS 10,398,381 B1 *  9/2019  Heneghan ............ A61B 5/0022
10,973,422 B2 *  4/2021  Pantelopoulos ... A61B 5/02416
(Continued)

FOREIGN PATENT DOCUMENTS

| KR | 20170096323 A | 8/2017 |
|---|---|---|
| WO | 2016137698 A1 | 9/2016 |
| WO | 2017063086 A1 | 4/2017 |

OTHER PUBLICATIONS

Emilio Vanoli, Philip B. Adamson, Ba-Lin, Gian D. Pinna, Ralph Lazzara, and William C. Orr, "Heart Rate Variability During Specific Sleep Stages", Apr. 1, 1995 (Year: 1995).*
(Continued)

*Primary Examiner* — Tse W Chen
*Assistant Examiner* — Clarissa Cuevas

(57) ABSTRACT

The present disclosure pertains to a method and system for determining the blood pressure dip of a subject based on features extracted from information generated by an on-body sensor system. The on-body sensor system includes a photoplethysmographic (PPG) sensor and a motion sensor. Blood pressure variation is captured throughout the day and utilized along with determinations of whether a subject is asleep or awake. The blood pressure determinations collected throughout the day, along with determinations of sleep periods, are used to determine a blood pressure dip for the day the on-body sensor system is worn.

6 Claims, 5 Drawing Sheets

(51) Int. Cl.
    *A61B 5/0295*  (2006.01)
    *A61B 5/00*    (2006.01)
    *A61B 5/021*   (2006.01)
(52) U.S. Cl.
    CPC .......... *A61B 5/02416* (2013.01); *A61B 5/681* (2013.01); *A61B 5/7264* (2013.01); *A61B 5/0295* (2013.01); *A61B 5/4809* (2013.01)

(56) References Cited

U.S. PATENT DOCUMENTS

| | | | | |
|---|---|---|---|---|
| 11,045,095 | B2* | 6/2021 | Tao | A61B 5/02416 |
| 2015/0164351 | A1* | 6/2015 | He | A61B 5/0285 |
| | | | | 702/19 |
| 2016/0029964 | A1* | 2/2016 | LeBoeuf | A61B 5/4266 |
| | | | | 600/476 |
| 2017/0055898 | A1* | 3/2017 | Bandyopadhyay | A61B 5/303 |
| 2018/0301224 | A1* | 10/2018 | Matichuk | A61B 5/4866 |
| 2018/0360325 | A1* | 12/2018 | Robinson | A61B 5/02427 |
| 2019/0104951 | A1* | 4/2019 | Valys | G16H 50/20 |
| 2019/0307337 | A1* | 10/2019 | Little | A61B 5/332 |

OTHER PUBLICATIONS

International Search Report and Written Opinion, International Application No. PCT/EP2019/056739, dated Mar. 19, 2019.
Shukla, S., "Estimation of Blood Pressure from Non-invasive Data", IEEE, 2017, pp. 1772-1775.
Yilmaz, T. et al., "Detecting Vital Signs with Wearable Wireless Sensors", Sensors, 2010.
Markets and Markets, Vital signs monitoring market—Landscape analysis of blood pressure monitoring devices, pulse oximeters and temperature monitoring devices—forecast up to 2018, 2013.
"Understanding Blood Pressure Readings", https://www.heart.org/en/health-topics/high-blood-pressure/understanding-blood-pressure-readings, Accessed Mar. 29, 2019.
"High Blood Pressure Facts", https://www.cdc.gov/bloodpressure/facts.htm, Accessed Mar. 29, 2019.
McGhee et al, Monitoring arterial blood pressure: What you may not know, Crit. Care Nurse, 2002.
Alpert et al, Oscillometric blood pressure: A review for clinicians, Am. Soc. Hypertension, 2014.
De la Sierra et al., Prevalence and Factors Associated With Circadian Blood Pressure Patterns in Hypertensive Patients, Hypertension, 2009, pp. 466-472.
Bloomfield et al, Night time blood pressure dip, World journal of cardiology, 2015, pp. 373-376.
Elgendi, On the analysis of fingertip photoplethysmogram signals, Current Cardiology Reviews, 2012.
Mukkamala et al, Towards ubiquitous blood pressure monitoring via pulse transit time: Theory and practice, IEEE transactions on biomedical engineering, 2015.
Proença et al., Is Pulse Transit Time a good indicator of Blood Pressure changes during short physical exercise in a young population?, IEEE conference EMBS 2010, 2010.
Monte-Moreno, Non-invasive estimate of blood glucose and blood pressure from a photoplethysmograph by means of machine learning techniques, Artificial Intelligence in Medicine, 2011.
Staessen et al, Task force II: blood pressure measurement and cardiovascular outcome, Blood Pressure Monitoring, 2001, pp. 355-370.
Peixoto et al., Circadian blood pressure: Clinical implications based on the pathophysiology of its variability, Kidney International, 2007, pp. 855-860.
Hermida, Bedtime Dosing of Antihypertensive Medications Reduces Cardiovascular Risk in CKD, J. AM Soc Nephrol, 2011.

* cited by examiner

SYSTEM AND METHOD FOR NON-INVASIVE DETERMINATION OF BLOOD PRESSURE DIP BASED ON TRAINED PREDICTION MODELS

CROSS-REFERENCE TO PRIOR APPLICATIONS

This application claims the benefit of U.S. Provisional Application 62/650,488, filed on 30 Mar. 2018. This application is hereby incorporated by reference herein.

BACKGROUND

1. Field

The present disclosure pertains to a system and method for monitoring blood pressure, and, non-invasively determining blood pressure dip based on trained prediction models.

2. Description of the Related Art

Measuring the variation of blood pressure throughout 24 hours of ambulatory blood pressure monitoring (ABPM) with an oscillometric blood pressure cuff that measures the blood pressure at specific intervals (e.g., every 30 minutes) is known. Over the course of 24 hours, these periodic blood pressure measurements have a negative effect on sleep quality, require several pauses in normal daily activity, are uncomfortable, and may be painful. This and other drawbacks exist.

SUMMARY

Accordingly, one or more aspects of the present disclosure relate to a system for determining blood pressure dip in a subject via machine learning models. The system comprises a wearable device configured to be worn by the subject. The wearable device comprises a photoplethysmographic (PPG) sensor configured to generate output signals conveying information related to a bloodflow of the subject and an accelerometer configured to generate output signals conveying information related to motion of the subject. The system includes one or more processors operatively coupled to the wearable device and configured by machine-readable instructions to receive output PPG signals from the PPG sensor over a period of time, and receive output motion signals from the accelerometer over the period of time. In some embodiments, the system is configured to determine, based on at least the PPG signals, one or more bloodflow features. The one or more bloodflow features indicate a variability of the bloodflow and/or a shape of a bloodflow curve over the period of time. In some embodiments, the system is configured to determine, based on the motion signals, a physical state of the subject. The physical state indicates whether the subject is awake or asleep. The system is configured to provide the one or more bloodflow features and the physical state to a machine learning model. The system is configured to cause the machine learning model to determine the blood pressure dip of the subject for the period of time based on at least the one or more bloodflow features and the physical state, and cause transmission of the blood pressure dip to the wearable device.

Another aspect of the present disclosure relates to a method for determining blood pressure dip in a subject via machine learning models. In some embodiments, the method is implemented by a wearable device configured to be worn by the subject and one or more processors operatively coupled to the wearable device. The wearable device includes a photoplethysmographic (PPG) sensor configured to generate output signals conveying information related to a bloodflow of the subject, and an accelerometer configured to generate output signals conveying information related to motion of the subject. The one or more processors are configured by machine readable instructions. In some embodiments, the method comprises: receiving, with the one or more processors, output PPG signals from the PPG sensor over a period of time, receiving, with the one or more processors, output motion signals from the accelerometer over the period of time, and determining, with the one or more processors, based on at least the PPG signals, one or more bloodflow features. In some embodiments, the one or more bloodflow features indicate a variability of the bloodflow and/or a shape of a bloodflow curve over the period of time. In some embodiments, the method includes determining, with the one or more processors, based on the motion signals, a physical state of the subject. The physical state indicates whether the subject is awake or asleep. The method comprises providing, with the one or more processors, the one or more bloodflow features and the physical state to a machine learning model. In some embodiments, the method includes causing, with the one or more processors, the machine learning model to determine the blood pressure dip of the subject for the period of time based on at least the one or more bloodflow features and the physical state, and causing, with the one or more processors, transmission of the blood pressure dip to the wearable device.

Still another aspect of present disclosure relates to a system for determining blood pressure dip in a subject via machine learning models. The system comprises means for generating output PPG signals over a period of time and means for generating output motion signals over the period of time. The means for generating output PPG signals and the means for generating output motion signals are included in a wearable device configured to be worn by the subject. The system comprises means for receiving output PPG signals from the PPG sensor over the period of time, means for receiving output motion signals from the accelerometer over the period of time, and means for determining, based on at least the PPG signals, one or more bloodflow features. In some embodiments, the one or more bloodflow features indicate a variability of the bloodflow and/or a shape of a bloodflow curve over the period of time. In some embodiments, the system includes means for determining, based on the motion signals, a physical state of the subject. The physical state indicates whether the subject is awake or asleep. The system includes means for providing the one or more bloodflow features and the physical state to a machine learning model. In some embodiments, the system includes means for causing the machine learning model to determine the blood pressure dip of the subject for the period of time based on at least the one or more bloodflow features and the physical state, and means for causing transmission of the blood pressure dip to the wearable device.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1A:
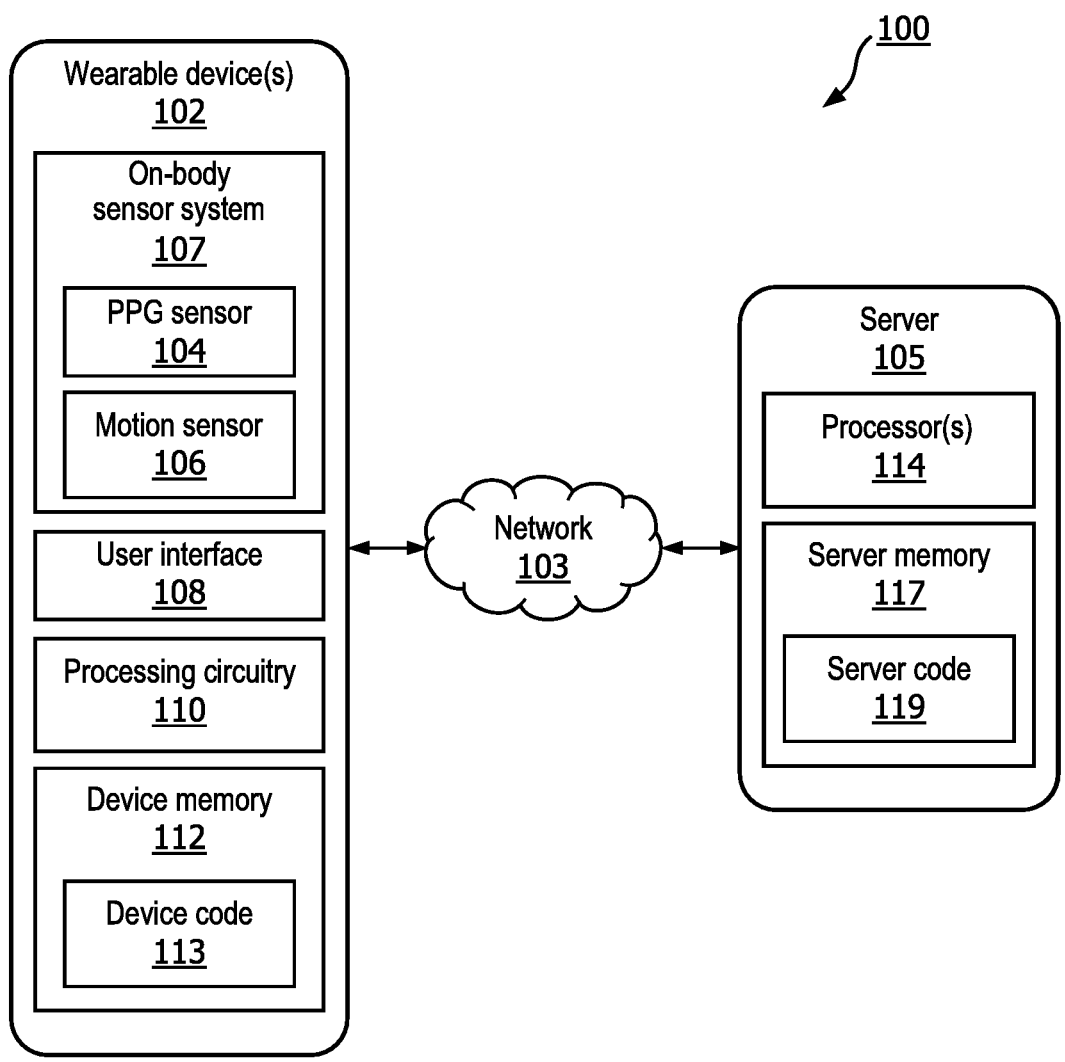
FIGS. 1A and 1B are schematic illustrations of a system for noninvasive determination of a blood pressure dip.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Ambulatory 24-hour blood pressure monitoring has become useful in the diagnosis and management of hypertensive subjects. The circadian blood pressure rhythm is associated with conditions of the cardiovascular system. Controlling the circadian blood pressure rhythm is important in managing hypertension and predicting cardiovascular outcome. Subjects with an insufficient amount of blood pressure decrease during night-time (or other sleeping times), and/or having an excessive morning (or other post-sleep times) blood pressure surge, are associated with increased risk of cardiovascular diseases.

The exemplary embodiments described herein offer a comfortable, easy, and unrestrained method to determine the blood pressure dip of the subject. For example, with the present system, a subject is not required to use a blood pressure cuff or other similar equipment at regular intervals. This is accomplished by means of a wearable device having an on-body sensor system, which the subject wears for 24 hour periods of time. An example 24 hour period may start from the moment a subject wakes up on a first morning until the moment the subject wakes up the next morning. The exemplary embodiments described herein determine a subject's blood pressure dip from captured sensor signals without the usage of an obtrusive, uncomfortable inflatable cuff that the subject has to wear for the entire day. Instead of requiring a subject to participate in regular physical blood pressure measurements throughout a given day (and/or other periods of time), the present system predicts the blood pressure of the subject and determines a corresponding blood pressure dip for the subject based on the output from the nonintrusive on-body sensor system using a prediction model (e.g., a machine-learning model as described below and/or other prediction models). In some embodiments, system 100 may decrease a need for electronic storage of daily recorded blood pressure values, may provide a continuous stream of sensor information that is used to more accurately (relative to prior art systems that made determinations based on information recorded at various intervals— e.g., 30 minute intervals) determine blood pressure and blood pressure dip, and/or have other advantages.

Some embodiments described herein determine a blood pressure dip by determining blood pressure variation throughout the day, while also monitoring whether the subject is awake or asleep. The blood pressure determined throughout the day, along with the information on daytime and nocturnal sleep periods, are used to determine a single blood pressure dip for the day the device is worn.

FIG. 1A schematically illustrates an exemplary embodiment of a blood pressure dip determination system 100. As shown in FIG. 1A, system 100 includes wearable device 102, network 103, server 105, and/or other components. In some embodiments, wearable device 102 is configured to communicate with server 105 via network 103 and/or by other methods. Server 105 is similarly configured to communicate, via network 103 and/or by other methods, with wearable device 102. In some embodiments, network 103 is implemented via a WAN/LAN network that is connected to the Internet via a hybrid fiber-optic cable (HFC) communication network provided by an Internet Service Provider (ISP). In some embodiments, communication between wearable device 102, server 105, and network 103 is implemented via a wireless communication network such as GSM, TDMA, CDMA, 3G, 4G, LTE, 5G, or any other wireless communication protocol capable of establishing an Internet connection. In some embodiments, the functionality of server 105 is provided by processing components (e.g., processing circuitry 110) of wearable device 102 and/or other components of the present system.

Figure 1B:
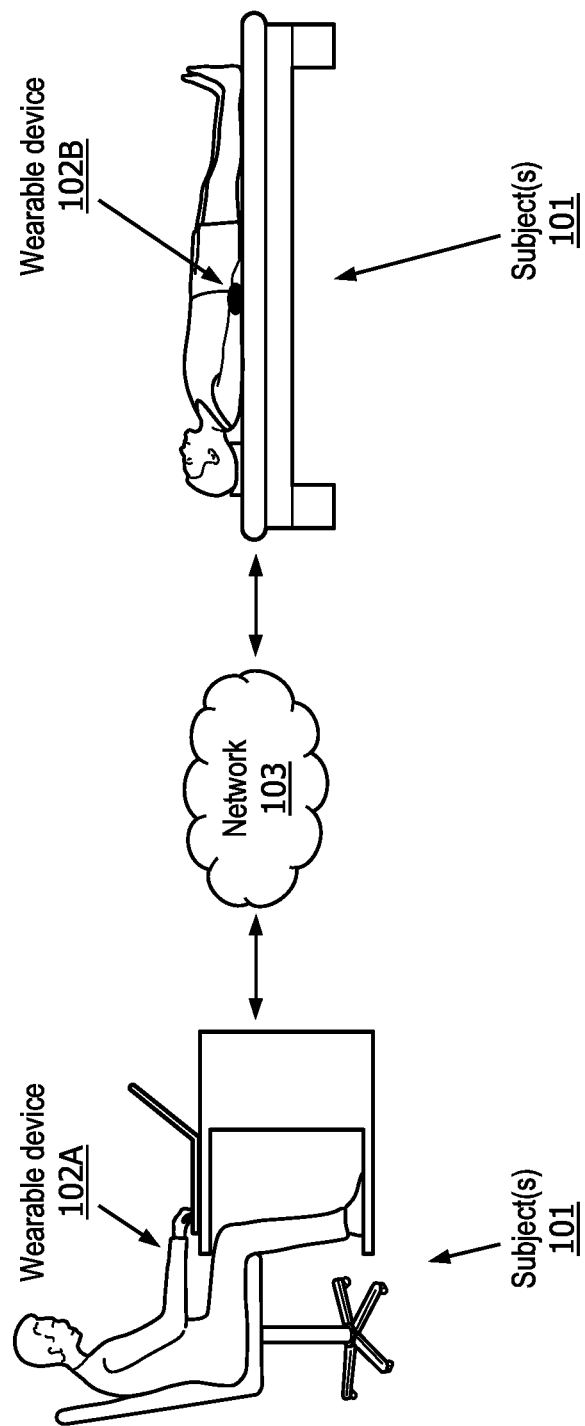

Referring now to FIG. 1B in conjunction with FIG. 1A, FIG. 1B illustrates a portion of system 100 of FIG. 1A including wearable devices 102 (e.g., devices 102A and 102B) and network 103. In some embodiments, wearable devices 102A and 102B are configured to be worn by subject(s) 101. Subject(s) 101 includes one or more subjects wearing wearable devices 102A and 102B. As shown in FIG. 1B, wearable devices 102A and 102B are configured to be worn by subjects 101 while sitting, lying down, and/or while performing other normal daily activities. Wearable device 102 (e.g., wearable device 102A, 102B, etc.) includes straps, clamps, hooks, clips, and/or other components configured to removably couple with one or more body parts (e.g., wrist, ankle, head, chest, etc.) and/or clothing of subject 101. As shown in FIG. 1B, in some embodiments, subject(s) 101 wears wearable device 102 on either wrist for at least a 24 hour period and/or other periods of time. For example, a 24 hour period may begin from the moment subject 101 wakes up and end the moment subject 101 wakes up the next day. In some embodiments, wearable device 102 (e.g., 102A, 102B, etc.) may be and/or include an Apple or Samsung smart watch, and/or other smart watches. In some embodiments, the wearable device 102 includes any other wearable device capable of transmitting a PPG signal indicative of the subject's bloodflow and a motion signal indicative of the subject's activity level.

As shown in FIG. 1A, in some embodiments, wearable device 102 comprises an on-body sensor system 107 including PPG sensor 104 and motion sensor 106, user interface 108, processing circuitry 110, memory 112 having device code 113 stored thereon, and/or other components. Processing circuitry 110 is configured to access memory 112 to execute device code 113 for carrying out the exemplary embodiments described herein.

In some embodiments, on-body sensor system 107 includes a sensor that captures a raw bio signal, and a sensor that outputs a signal that is indicative of the subject's physical activity level. In some embodiments, on-body sensor system 107 includes PPG sensor 104 and motion sensor 106, and/or other sensors. In some embodiments, the raw bio signal is and/or is related to a PPG signal. Motion sensor 106 is configured to output, via processing circuitry 110, a motion signal that is indicative of the subject's level of activity to server 105 and/or other computing devices. PPG sensor 104 is similarly configured to output a PPG signal to server 105 and/or other computing devices, via processing circuitry 110. In some embodiments on-body sensory system 107 includes any other bio sensor suitable to register changes in bloodflow and/or capture heart rate variability of the subject, for example: microphone(s), bio-impedance sensor(s), ECG sensors, remote camera(s) that captures variations in skin tone representing blood volume changes, acceleration sensor(s) measuring precordial acceleration, bed sensor(s) utilized in ballistocardiogram, audio sensors and/or ultrasound sensors used for echocardiogram, low pressure sensors, tonometry sensors, and/or tomography sensors In some embodiments, PPG sensor 104 is an optic sensor configured as a blood pulse volumetric sensor. In blood pulse volumetric sensing, the amount of reflected light detected by PPG sensor 104 during each cardiac cycle varies as more or less blood flows through the arterioles of the subject. PPG sensor 104 utilizes pulse-oximetry concepts to track the bloodflow volume of the subject. Pulse oximetry tracks the average skin tone, which varies with blood volume and blood oxygenation. This variation in skin tone over time contains information on the blood volume. In some embodiments, PPG sensor 104 is configured to convert the reflected light into an electrical signal, which tracks the average skin tone. In some embodiments, PPG sensor 104 operates in a reflective mode. In reflective mode, PPG sensor 104 shines LED light on the subject's skin surface and measures the amount of light that is backscattered or reflected by the skin tissue, bone, and/or blood vessels. In some embodiments, PPG sensor 106 operates in a transmission mode. In transmission mode, the light transmitted through the medium is detected by a photodiode opposite to the LED source In some embodiments, the LED light is implemented by means of a photodiode (not shown in FIG. 1A). In some embodiments, the LED is a wavelength corresponding to green light. Other optical transistors that are configured to reflect an optical signal and convert the reflected optical signal to an electrical signal may also be implemented without diverting from the scope and spirit of the exemplary embodiments presented herein.

In some embodiments, motion sensor 106 is and/or includes an accelerometer configured to generate output signals conveying information related to motion of the subject. In some embodiments, motion sensor 106 is a 3-axis accelerometer configured to sense motion on 3 axes. The motion signal is indicative of the subject's activity level. While a 3-axis accelerometer is described herein, other means for measuring motion may be implemented without diverting from the scope and spirit of the embodiments described herein.

In some embodiments, processing circuitry 110 is configured to transmit the electrical PPG signal output by PPG sensor 104, along with the output signal of motion sensor 106. Accordingly, PPG sensor 104 and motion sensor 106 are configured to communicate PPG signals and motion signals to server 105 and/or other devices via processing circuitry 110 and/or other components. As discussed in further detail below, server 105 is configured to receive motion signals and PPG signals and determine a blood pressure dip of the subject. As discussed below, in some embodiments, processors(s) 114 is configured to access server memory 117 to execute server code 119 to determine and transmit the blood pressure dip determination to wearable device 102 for display via user interface 108. In some embodiments, the operations performed by server 105 may be performed by processing circuitry 110 and/or one or more processors that may be in included in wearable device 102.

In some embodiments, user interface 108 is an LCD screen of a smart watch or other graphic user interface capable of communicating information to, and receiving information from, a subject. User interface 108 is configured to provide an interface between system 100 and the subject, and/or other subjects through which the subject and/or other subjects may provide information to and receive information from system 100. This enables data, cues, results, and/or instructions and any other communicable items, collectively referred to as "information," to be communicated between the subject and one or more components of system 100.

Examples of interface devices suitable for inclusion in user interface 108 comprise a keypad, buttons, switches, a keyboard, knobs, levers, a display screen, a touch screen, speakers, a microphone, an indicator light, an audible alarm, a tactile feedback device, and/or other interface devices. In some embodiments, user interface 108 comprises at least one interface that is provided integrally with processing circuitry 110 and/or other components of system 100. It is to be understood that other communication techniques, either hard-wired or wireless, are also contemplated by the present disclosure as user interface 108.

Device memory 112 comprises electronic storage media that electronically stores information. The electronic storage media of device memory 112 may comprise one or both of system storage that is provided integrally (i.e., substantially non-removable) with wearable device 102 and/or removable storage that is removably connectable to wearable device 102 via, for example, a port (e.g., a USB port, a firewire port, etc.) or a drive (e.g., a disk drive, etc.). Device memory 112 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Device memory 112 may store software algorithms (e.g., device code 113), information determined by processing circuitry 110, information received via user interface 108 and/or external computing systems (e.g., server 105), and/or other information that enables system 100 to function as described herein.

Figure 2A:
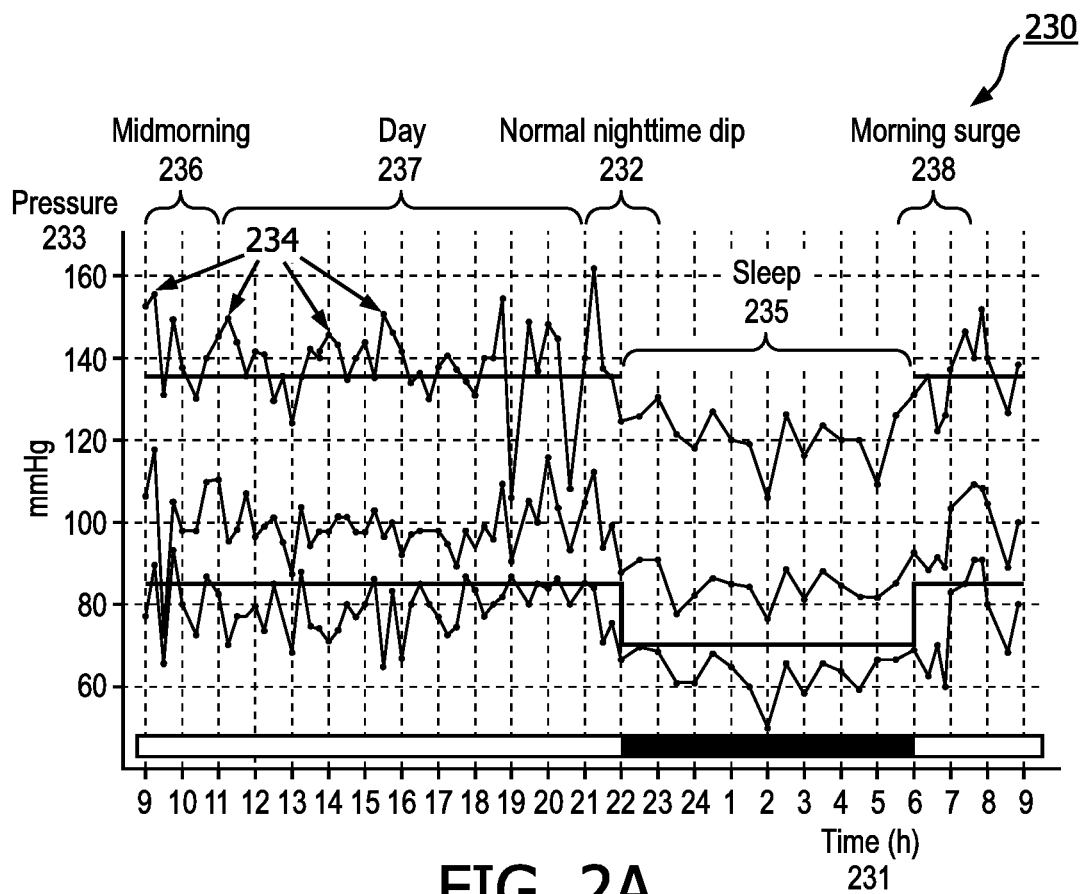
FIGS. 2A and 2B are schematic illustrations of exemplary 24-hour ambulatory blood pressure readings.
Figure 2B:
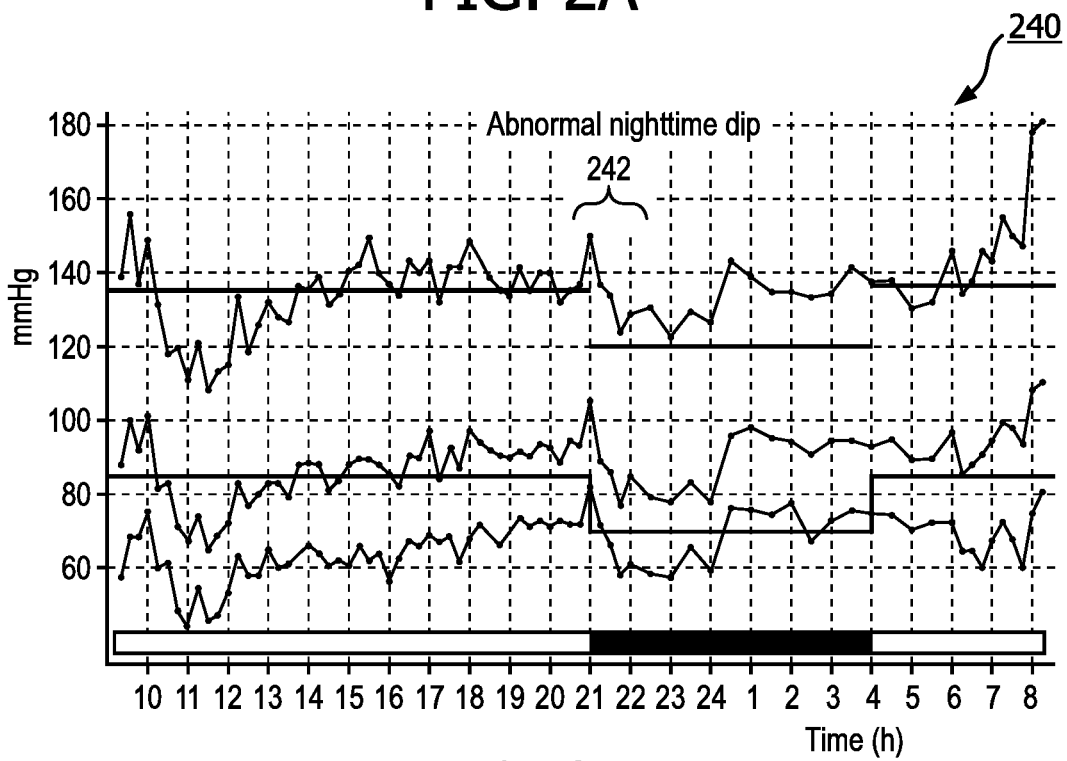

Referring now to FIGS. 2A and 2B, FIG. 2A depicts an ambulatory blood pressure recording 230 of a 24 hour period of time 231 for a subject, showing a normal nighttime dip 232. As shown in FIG. 2A blood pressure 233 has a daily variation 234 and typically decrease during sleep 235. Usually the blood pressure is highest midmorning 236, and then reduces progressively throughout the rest of the day 237. In addition, blood pressure is often the lowest at night during sleep 235 and rises before awakening, known as the morning surge, shown in FIG. 2A as morning surge 238. In normotensive subjects, the natural circadian rhythm blood pressure includes a nocturnal decrease of 10-20% blood pressure, for example.

Referring now to FIG. 2B, FIG. 2B depicts another ambulatory blood pressure recording, and specifically a typical non-dipping blood pressure pattern 240. As shown in FIG. 2B, non-dipping blood pressure pattern 240 includes abnormal nighttime dip 242, which is an example of a non-dipping blood pressure pattern. Non-dipping is associated with a greater risk of cardiovascular compilations, including stroke. Also, non-dipping is associated with sleep disturbances, OSA, obesity, age, orthostatic hypotension, autonomic dysfunction, chronic kidney disease, and diabetic neuropathy. Each 5 mmHg of nocturnal blood pressure decrease is associated with a 14% reduction in cardiovascular risk, for example. Unusual circadian blood pressure patterns can be caused by intrinsic factors such as abnormalities in sympathetic nervous system activity, and more extrinsic factors like physical activity level, shiftwork, high salt intake and volume balance, for example. These factors can be modified by lifestyle, dietary changes and/or administering antihypertensive drugs to correct for abnormal circadian rhythms. Antihypertensive drugs before sleep may restore the dipping status in non-dippers.

In some embodiments, the blood pressure dip is determined according to the following equation:

$$BPdip = \frac{\text{average daytime } BP - \text{average night time } BP}{\text{average daytime } BP} * 100\%$$

In some embodiments, other statistics of the 24 hour ambulatory blood pressure readings are determined, including but not limited to blood-pressure variability, hyperbaric area index, minimum nocturnal blood pressure, morning surge, and/or other ambulatory blood pressure readings.

In some embodiments blood pressure variability is determined by measuring a fluctuation in blood pressure in the 24 hour ambulatory blood pressure cycle. In some embodiments, measuring the fluctuation in blood pressure includes determining the standard deviation between measurements, or determining the standard deviation between successive differing blood pressure measurements. In some embodiments, the hyperbaric area index, also known as blood-pressure load, is determined as a measure of the time. The measure of time tracks the magnitude of moments that the blood pressure is too high, or above a desired blood pressure level. In some embodiments hyperbaric area index is determined by subtracting the cutoff values for high blood pressure from the signal and then to calculate the area under the signal where the blood pressure is above the cutoff value (i.e., where the blood pressure is too high). In some embodiments the morning surge is calculated or determined by analyzing the increase in blood pressure in the first 2 hours of wake up compared to baseline measures from the last day. In some embodiments, the minimal nocturnal blood pressure is determined from analyzing the minimal blood pressure during the sleep period.

Blood pressure is usually measured as two readings: systolic and diastolic pressure. Systolic pressure occurs in the arteries during the maximal contraction of the left ventricle of the heart. Diastolic pressure refers to the pressure in arteries when the heart muscle is resting between beats and refilling with blood. Normal blood pressure is considered to be less than 120/80 mmHg. Commonly the following categories of blood pressure dip are known:

(1) dipping: reduction in average systolic blood pressure (SBP) and diastolic blood pressure (DBP) at night, which is greater than 10% and less than 20% compared with average daytime values;

(2) non-dipping: nocturnal reduction in average SBP and DBP less than 10%. Patients with hypertension having increased adrenergic and decreased vagal activity during sleep;

(3) extreme dipping: reduction in average SBP and DBP at night greater than or equal to 20%. Closely associated with increased white matter ischemic lesions in the brain and excessive morning blood pressure surge; and (4) reverse dipping: patients with high nocturnal average SBP and DBP in comparison with eternal values.

In some embodiments, the determined blood pressure dip is characterized as one of either: dipping, non-dipping, extreme dipping, or reverse dipping, in accordance with the descriptions above.

Figure 3:
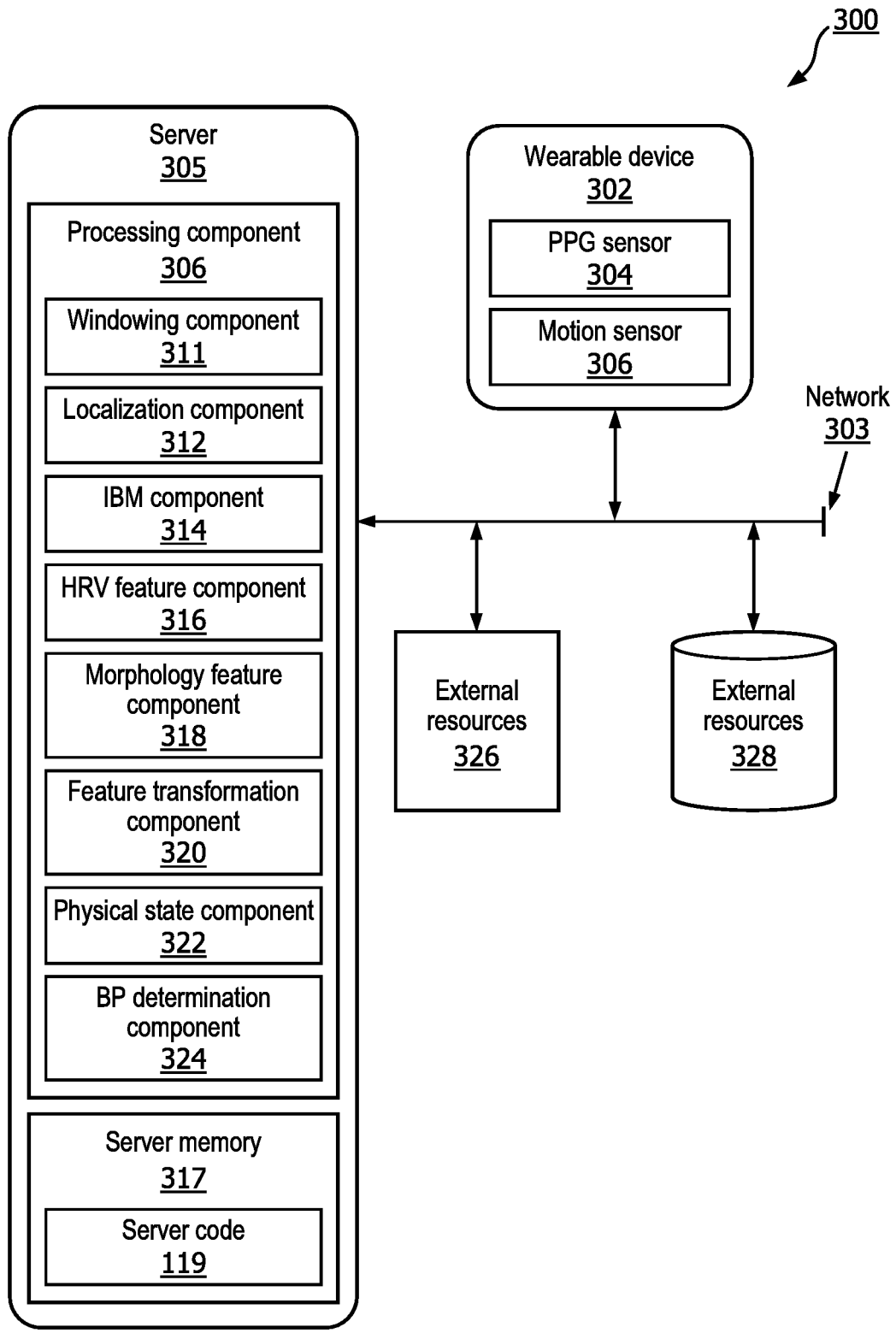
FIG. 3 is a schematic illustration of an exemplary embodiment of the system for noninvasive determination of blood pressure dip of FIG. 1.

Referring now to FIG. 3, FIG. 3 depicts an exemplary system 300 configured for determining blood pressure dip in a subject via prediction models. System 300 is an exemplary embodiment of system 100 of FIG. 1A, of which similarly labeled numbers and parts correspond to similar structure and functionality (e.g., server 305 is similar to and/or the same as server 105, wearable device 302 is similar to and/or the same as wearable device 102, and network 303 is the same as or similar to network 103). System 300 includes wearable device 302, server 305, network 303, external resources 326, and electronic storage 328. As shown in FIG. 3, in some embodiments, server 305 includes processor component 306, and server memory 317 having server code 319 stored thereon.

In some embodiments, server 305 includes processing component 306, which is configured via machine-readable instructions (e.g., server code 319) to execute one or more computer program components. The one or more computer program components may comprise one or more of windowing component 311, localization component 312, inter-beat-interval (IBI) component 314, heart rate variability (HRV) feature component 316, morphology feature component 318, feature transformation component 320, physical state component 322, blood pressure (BP) determination component 324, and/or other components. Processing component 306 may be configured to execute components 311, 312, 314, 316, 318, 320, 322, or 324 by software; hardware; firmware; some combination of software, hardware, or firmware; or other mechanisms for configuring processing capabilities on processing component 306.

It should be appreciated that although components 311, 312, 314, 316, 318, 320, 322, and/or 324 are illustrated in FIG. 3 as being co-located within a single processing unit, in embodiments in which processing component 306 comprises multiple processing units, one or more of components 311, 312, 314, 316, 318, 320, 322, and/or 324 may be located remotely from the other components. The description of the functionality provided by the different components 311, 312, 314, 316, 318, 320, 322, and/or 324 described below is for illustrative purposes, and is not intended to be limiting, as any of components 311, 312, 314, 316, 318, 320, 322, and/or 324 may provide more or less functionality than is described. For example, one or more of components 311, 312, 314, 316, 318, 320, 322, and/or 324 may be eliminated, and some or all of its functionality may be provided by other components 311, 312, 314, 316, 318, 320, 322, and/or 324. As another example, processing component 306 may be configured to execute one or more additional components that may perform some or all of the functionality attributed below to one of components 311, 312, 314, 316, 318, 320, 322, and/or 324. In some embodiments, the functionality of one or more of these components may be provided by processing components (e.g., processing circuitry 110) of wearable device 102 shown in FIG. 1A and/or other components of the present system.

In some embodiments, windowing component 311 is configured to receive output PPG signals from PPG sensor 304 over a period of time and receive output motion signals from motion sensor 306 over the period of time. In some embodiments, the period of time is a continuous 24-hour period of time. For example, the 24-hour period starts from the moment the subject wakes up to the next time the subject wakes up the next day. In other embodiments the period of time is longer or shorter than 24 hours.

In some embodiments, windowing component 311 is configured to receive PPG signal and motion data and process both signals into discrete epochs. Epochs are a predetermined amount of PPG signal and motion data. In some embodiments, discrete epochs are 30 seconds of PPG signal and motion data. In some embodiments, the epoch are sliding windows with a predetermined length and overlap of 30 seconds. In some embodiments, the epoch size or length of the sliding window is determined by the type of features extracted (e.g., HRV features/morphology features, discussed further below). In some embodiments, the window length for HRV feature extraction is 270 seconds. In some embodiments the window length for morphology feature extraction is 60 seconds. In some embodiments, other window lengths are utilized for various feature extractions (e.g., PPG signal and motion feature extraction.

In some embodiments, windowing component 311 is configured to buffer the incoming PPG signal and motion data in 30 second intervals and output the buffered PPG signal and/or motion data once the data buffer has 30 seconds of motion and PPG signal data. In some embodiments, the data buffer is a first in first out (FIFO) buffer configured to receive motion data and/or PPG signal data. In some the intervals may be more or less than 30 seconds.

In some embodiments, windowing component 311 is also configured to process the raw PPG signal and motion signal for removing high frequency noise reduction and low frequency artifact. In some embodiments, removing high/low frequency noise and artifact is implemented via a smoothing function, which is configured to smooth out the noise within the signal. Other implementations for noise and artifact removal may be implemented without diverting from the scope and spirit of the embodiments presented herein.

In some embodiments, localization component 312 is configured to localize in the PPG signal the beat onset of each cardiac cycle. Localizing the beat onset of each cardiac cycle includes performing time translations of portions of the PPG signal to align the portions of the PPG signal similarly in time for further processing. In addition to localizing the PPG signal, in some embodiments, localization component 312 is configured to reject low-quality beats based on the morphology of the PPG pulses (e.g., ambient light) and registered motion (e.g., motion artifact) represented by the motion signal.

In some embodiments, localizing the PPG signal and rejecting low quality heartbeats is performed in a manner that does not look for specific landmarks within the PPG signal. Stated another way, system 300 is implemented in a manner that does not look for specific points in the PPG signal, the morphology features, or in the HRV feature extraction process, which are discussed in further detail below. Rather, the exemplary embodiments described herein looks at the morphology of the PPG signal as a whole to determine both high-quality heartbeats and morphology/HRV feature extraction.

In some embodiments, beat detection may include detection of specific landmarks present in the PPG signal. In some embodiments, landmarks include the location of the PPG minimum (i.e., foot), the location of the PPG maximum (i.e., peak), and/or the location of the maximum positive amplitude and the $2^{nd}$ derivative of the PPG signal (i.e., onset). In some embodiments, the interval defined by 2 consecutive (foot) landmarks typically describes a complete cardiac cycle. In some embodiments, parametric methods such as wavelet transformation and/or hyperbolic tangent fitting are utilized for determining heartbeats in the PPG signal.

In some embodiments, determining one or more bloodflow features indicating the shape of the bloodflow curve over the period of time includes first rejecting low quality heartbeats contained in the PPG signal. In some embodiments, rejecting low quality heartbeats is determined by analyzing the PPG morphology or the shape of the PPG signal, and comparing the shape of the PPG signal to an expected or anticipated shape of the PPG signal.

In some embodiments, rejecting low-quality beats includes determining one or more bloodflow features of the subject by determining a PPG morphology of a portion of the PPG signal, and determining an anticipated shape of the portion of the PPG signal. In some embodiments, server 305 is configured to access a databank of known PPG morphology data sets, which are utilized for determine an anticipated shape of high quality heartbeats. In some embodiments, anticipated shapes and/or morphologies of high quality heartbeats are stored in electronic storage 328. In some embodiments, the anticipated morphologies and/or shapes are provided by a third party, for example via external resources 326. In some embodiments, the anticipated morphology shape is determined by accessing a user template stored in electronic storage 328 or external resources 326. In some embodiments, a user template is recorded during an offline stage, which is discussed in further detail below. The user template includes a high quality PPG signal, which can be used as a reference for rejecting low quality beats.

In some embodiments, responsive to the PPG morphology corresponding to the anticipated shape of the PPG morphology, localization component 312 may output that portion of the PPG signal to IBI component 314. IBI component 314 then determines the an inter-beat-interval time series outputs the IBI interval time series to HRV feature component 316 for determining, the one or more bloodflow features of the subject.

Accordingly, in some embodiments, the portion of the PPG signal is utilized for determining the one or more bloodflow features of the subject responsive to the PPG morphology corresponding to the anticipated shape of the PPG morphology. PPG morphology corresponding to the anticipated shape of the PPG morphology means that PPG morphology matches the anticipated shape. Matching may not necessarily require an exact match but rather a predetermined degree of matching, which is determined through heuristic testing, as is known in the art. In some embodiments, in order to measure the similarity between the morphology of the PPG signal or a particular PPG epoch and the morphology corresponding to the anticipated shape of the PPG morphology (e.g. stored as a user template, which is described in detail below), the following procedure could be used. First, align the current PPG epoch and the anticipated morphology/template by applying a dynamic time warping function. Dynamic time warping allows alignment of two time dependent sequences. Once the PPG epoch and anticipated morphology/template are time aligned, a distance function is applied to quantify the similarity (e.g., Euclidian distance). The distance between the PPG epoch and anticipated morphology/template is compared against a pre-defined threshold to determine whether the morphology matches the anticipated shape In some embodiments, localization component 312 utilizes the motion signal output by motion sensor 306 in order to reject low-quality heartbeats. In some embodiments, rejecting low quality heartbeats is performed by analyzing the motion signal output by motion sensor 306 to detect motion artifact in the PPG signal. If the detected motion artifact exceeds a predetermined threshold, the portion of the PPG signal is rejected as low quality beats. If the motion level does not exceed the threshold level, then that portion of the PPG signal is sent to IBI component 314 and HRV feature extraction component 316 for further processing as described herein. Accordingly, in some embodiments, localization component 312 is configured for determining a motion level of the subject corresponding in time to a portion of the PPG signals, and determining, utilizing the portion of the PPG signals, the one or more bloodflow features of the subject, responsive to the motion level corresponding to less than a predetermined motion level.

As discussed above, in some embodiments, IBI component 314 utilizes the detected high-quality beats from the localization component 312 and converts the detected beats into an inter-beat interval time series. The inter-beat interval time series is a measure of the period between successive heartbeats for one or more pairs of successive heartbeats within the portion of the PPG signal, or the PPG epoch/window frame. In some embodiments, the inter-beat interval time series signal is output by IBI component 314 and received as input by the HRV feature component 316. As discussed in further detail below, in some embodiments, processing component 306 is configured to determine, based on at least the PPG signals, one or more bloodflow features, the one or more bloodflow features indicating a variability of the bloodflow and/or a shape of a bloodflow curve over the period of time.

In some embodiments, HRV feature component 316 is configured to determine, based on the PPG signals, a heart rate variability of the subject over the period of time. In some embodiments, the HRV of the subject over the period of time corresponds to the inter-beat-interval time series for the respective PPG epoch or window frame. In some embodiments, HRV feature component 316 is configured to receive as input the IBI time series signal output by IBI component 314, and extract a feature set from the IBI time series for the purpose of blood pressure determination. The feature set extracted from the IBI time series corresponds to heart rate variability features, which indicate changing characteristics of the heart rate variability over time. Accordingly, in some embodiments, HRV feature component 316 is configured for determining, based on the HRV, a plurality of HRV features, the HRV features indicating changing characteristics of the heart rate variability over the period of time.

In some embodiments HRV features are categorized into at least 3 different classes including time domain linear features, frequency features, and nonlinear features describing irregularly of the IBI series. In some embodiments time domain linear features include physical features such as minimum, maximum, mean, standard deviation percentiles, etc. In some embodiments, frequency features include features obtained by utilizing frequency band power analysis, for example utilizing the obtained coefficients when applying and autoregressive parametric spectral density (PSD) estimation. In some embodiments nonlinear features are determined by applying techniques such as but not limited to, detrending fluctuation analysis (DFA), and multiscale entropy (MSE). DFA is a technique that identifies long-range correlations within a signal, which is also useful when the signal has nonstationary characteristics. MSE timeseries analysis enables the assessment of complexity at shorter and longer timescales, and the quantification of the overall complexity of the system. As the sum of entropy values across all of the individual timescales.

In some embodiments, HRV features are extracted from the IBI time series using Hidden Markov Models (HMMs), similar to morphology feature extraction, which is discussed in further detail below.

In some embodiments, morphology feature component 318 is configured for morphology feature extraction for blood pressure predictions. In some embodiments, after low quality beats have been rejected, the extracted beats of the PPG signal are input to morphology feature component 318. In some embodiments, morphology feature component 318 determines a morphology feature based on both the signal output by windowing component 311 and the PPG signal output by the localization component 312. By using both the extracted high-quality localized cardiac cycles of the localization component 312 and the PPG signal from windowing component 311, morphology component 318 has a reference for extracting features only from the portion of the PPG signal that has high-quality heartbeats. In this manner the accuracy of morphology feature extraction is increased. Thus, increasing the accuracy of the blood pressure dip determination. Accordingly, in some embodiments, morphology component 318 is configured to determine, based on the PPG signals, a plurality of PPG morphology features, the morphology features indicating changing characteristics of the shape of the bloodflow curve over the period of time.

In some embodiments, morphology features are extracted directly from a portion of the PPG pulse, and consist of signal processing techniques to quantify entropy, irregularity, and frequency content of the PPG signal as a whole. In some embodiments morphology features are landmark base features. The landmark based features quantify specific morphological properties within a single PPG beat interval, such as the PPG foot, max amplitude and locations of certain inflection points of the PPG shape. In some embodiments, morphology features are parametrizations of the PPG shape, which are determined by decomposing the PPG shape into, for example, a set of Gaussian functions. The obtained amplitude and relative positions of the found sub-waves serve as morphology features. In some embodiments as discussed in detail below HRV/morphology/motion features are derived by prediction models. For example a neural network is implemented to learn a set of convolutional and/or timer current operations that would yield a comparable representation of the signal similar to the features as discussed above.

In some embodiments, extracting morphology features includes using Hidden Markov Models (HMMs). HMMs facilitate modeling time-varying spectral vector sequences. Feature extraction using HMMs comprises implementing a variety of wavelet transformation, frequency matching, and spectral analysis to extract feature vectors. In some embodiments, feature vectors are extracted every 10 ms (for example) using an overlapping analysis window of around 25 ms (for example).

Utilizing HMMs, each 30 second portion of the PPG signal is decomposed into a sequence of feature vectors. While HMMs are suited for feature extraction of features vectors for determining changing characteristics of the PPG signal over a period of time, other methods of feature extraction are known in the art and may be utilized without departing from the scope and spirit of the present disclosure.

In some embodiments, the HRV feature component 316 and morphology component 318 are configured to communicate their respective output signals to feature transformation component 320. Feature transformation component 320 is configured to receive both feature sets from HRV feature component 316 and morphology feature component 318 as input to a processing block that applies feature normalization and transformation to reduce amplitude variation. In some embodiments, normalization is implemented as a function that repeats the variation of signal so that outliers in the signal are amplified greatly and will stay amplified. In this manner, the amplitude of the signal is reduced while still maintaining the variation between successive sampling points in the signal.

In some embodiments, feature transformation component 320 is configured to merge the HRV feature set and the morphology feature set and output a transformed feature set to blood pressure determination component 224. In some embodiments, merging HRV and morphology feature sets includes extending a first feature set (e.g., HRV features) with a second feature set (e.g., morphology features) and normalizing each individual feature of the combined set. In some embodiments, instead of normalizing features, batch normalization is implemented as part of a neural network function for normalizing outputs of the deep neural layers rather than the features. In some embodiments, further feature transformation techniques are implemented on the combined HRV and morphology feature set such as: principal component analysis (PCA), multidimensional scaling (MDS), singular value decomposition (SVD), independent component analysis (ICA), and/or other feature transformation techniques. In some embodiments feature selection methods are utilized for reducing the feature space. For example, in some embodiments utilizing the embedded layers of a neural network, features may be transformed to a different feature space with desirable properties.

Blood pressure determination component 224 is configured to determine the blood pressure for particular 30 second (for example) windows of PPG signal data, or a PPG epoch, via a prediction model, which is discussed in detail below. In some embodiments, blood pressure determination component 224 is configured to aggregate the 30 second windows of PPG signal data throughout a 24 hour period to determine a blood pressure dip for the day. In some embodiments, determining the blood pressure dip for the day is also based on the physical state (e.g., asleep or awake) of the subject.

In some embodiments, physical state component 322 is configured to determine, based on the motion signals, a physical state of the subject, the physical state indicating whether the subject is awake or asleep. In some embodiments, physical state component 322 receives a motion signal output from windowing component 311, (i.e., a 30 second window of motion data). In some embodiments, physical state component 322 is configured to extract motion features from the motion data. In some embodiments, motion features include the instantaneous motion characteristics such as the number of zero crossings, periodicity, vertical acceleration, and motion cadence, and/or other motion features. In some embodiments, motion data feature extraction is performed in a similar manner as morphology feature extraction as discussed above. For example, by utilizing HMMs or neural networks having long-short memory structures implemented in a similar manner as HMMs. In some embodiments motion features are extracted using prediction models as discussed below.

In some embodiments, physical state component 322 is configured to process the PPG signal data and extract HRV features in a similar manner as performed by HRV feature component 316 discussed above (e.g., via localization component 312 and IBI component 314). In some embodiments, physical state component 322 is configured to normalize and merge the motion feature set and the HRV feature set and into a single feature set utilized for determining the physical state of the subject. In some embodiments, normalization and merging of the motion data feature set and the HRV feature set is implemented in a similar manner as performed by feature transformation component 320, as discussed above.

In some embodiments, physical state component 322 is configured to determine a physical state of the subject by determining an entropy gradient of the subject based on the merged motion and HRV feature sets. Entropy comprises a measure of irregularity for the heartrate. In some embodiments, entropy decreases as the heartrate becomes more regular, which is reflected in the HRV features of the combined feature set over time. Entropy typically decreases, and the heartrate becomes more regular, while the subjects is asleep, which is also reflected in the motion features of the combined feature set over time. The entropy can be determined based on the inter-beat-interval time series, the heart rate variability, determination of various HRV features and motion features, and/or other information. When the entropy is increasing, this correlates to the heartrate and IBI time series becoming more irregular. In some embodiments, determining an entropy of the subject is based on a measure of irregularity utilizing the HRV features extracted from the IBI time series. In some embodiments, determining the entropy includes utilizing the approximate entropy (ApEn), which is a technique used to quantify the amount of regularity and the unpredictability of fluctuations over time series data.

In some embodiments, physical state component 322 is configured to determine an entropy gradient of the subject utilizing the plurality of HRV features and the motion signals in an ongoing manner over the period of time. In some embodiments, physical state component 322 is configured to determine that the physical state is an awake state responsive to the entropy gradient decreasing (e.g., from epoch of time to the next). In some embodiments, physical state component 322 is configured to determine the physical state is an asleep state responsive to the entropy gradient increasing (e.g., from one epoch of time to the next). In some embodiments classifying the epochs for distinguishing sleep and awake states is based utilizing a pre-trained Bayesian-linear-discrimination functions on the combination of motion and HRV features. In some embodiments, classifying of sleep/awake epochs is solely based on motion features, HRV features, and/or the combination thereof. In some embodiments, physical state component 322 is configured to classify individual timeframes or epochs as either awake or asleep. The assigned classes are input into BP determination component 324 for determining a blood pressure dip for a 24 hour period.

In some embodiments, BP determination component 324 includes a BP prediction model, which is trained in an offline training stage (described below). In some embodiments, external resources 326 includes the BP prediction model, and BP determination component 324 is configured to access BP prediction model via external resources 326. In some embodiments, BP determination component 324 is configured to provide information to and/or receive information from the BP prediction model. In some embodiments, the BP prediction model is and/or includes machine learning models and/or algorithms, neural networks, and/or other prediction models. In some embodiments, external resources 326 includes sample data for training the BP prediction model. In some embodiments, sample data is collected from a number of sources including third party proprietary sources of data. In some embodiments, BP determination component 324 is and/or includes the BP prediction model.

In some embodiments, BP determination component 324 is configured to provide the one or more bloodflow features and the physical state classifications to the prediction model to cause the prediction model to predict the blood pressure and the blood pressure dip of the subject for the (e.g., 24 hour) period of time based on at least the one or more bloodflow features and the physical state classifications.

Figures 4, 5:
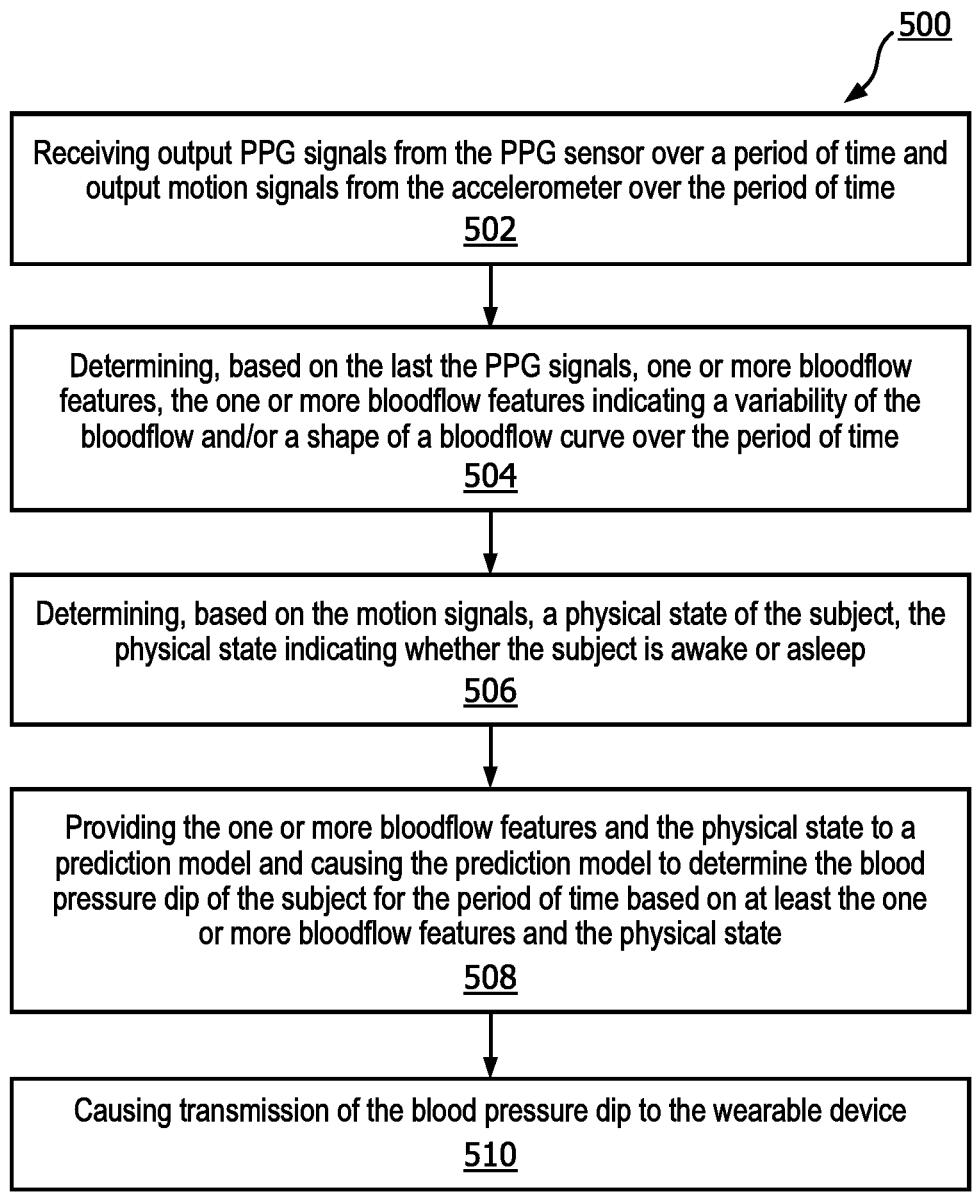
FIG. 4 is a schematic illustration of a predictive model used for predicting blood pressure of a subject.
FIG. 5 illustrates a method for implementing non-invasive blood pressure determination in accordance with one or more embodiments.

Referring now to FIG. 4 in conjunction with FIG. 3. FIG. 4 depicts an exemplary embodiment for training the BP prediction model. As shown in FIG. 4, FIG. 4 depicts an exemplary prediction model 424 in communication with external resources 426. Prediction model 424 is configured to operate in an offline training mode and access external resources 426 for obtaining training data for training prediction model 424. Training data is only used during the offline training mode and is not utilized in an online operational mode (e.g., the operations performed by system 100 described herein).

In some embodiments, the prediction model 424 comprises one or more neural networks, machine learning models and/or algorithms, and/or other prediction models, which are trained and utilized for generating blood pressure and blood pressure dip predictions. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together.

In some embodiments, each connection (or the neural unit itself) may have a threshold function such that the signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion. In some embodiments, the prediction models are trained during an offline stage using external resources 426.

In some embodiments, training the prediction model includes acquiring blood pressure readings with known and verified blood pressure values. External resources 426 includes a training database utilized for training prediction model 424. In some embodiments, prediction model 424 is configured to query external resources 426 to retrieve prediction model training data. Prediction model training data may include PPG signal data with known blood pressure values from a number of sources (e.g., healthcare/medical websites, medical journals, online libraries and databases, medical care facilities, and other sources of PPG data samples having known blood pressure values). In some embodiments, after retrieving the prediction model training data, training begins by first extracting features from the prediction model training data.

In some embodiments, training data feature extraction is performed in a similar manner as discussed above, for example similar to the morphology feature extraction and HRV feature extraction performed by HRV feature component 316 and morphology feature component 318, respectively. In some embodiments, morphology features are extracted from the training data as well as HRV features. In some embodiments, the morphology feature set and HRV feature set extracted from the training data are merged and combined into a single training feature. Merging and combining the feature sets are performed in a similar manner as discussed above. The resulting single training features set is implemented as input into prediction model 424 and mapped to corresponding output of known blood pressure values stored in external resources 426. In some embodiments prediction model 424 is configured include demographic information corresponding to the training data sample.

In some embodiments, training prediction model 424 is performed by developing optimized weight matrices so that during an operational mode for blood pressure prediction, the inputs and weights will cause prediction model 424 to predict the blood pressure level of the subject. In some embodiments, inputs for training prediction model 424 includes feature vectors extracted from the training data. In some embodiments, feature vectors correspond to changing characteristics of the PPG signal. In some embodiments, prediction model 424 is trained when outputs generated by the neural network for a given input feature vector are compared with the expected output. In some embodiments the prediction model utilizes long and short-term memory (LSTM), gated recurrent units (GRU), convolution neural architectures (dilated, strided, residual-based, skipped, causal), regularization techniques such as dropout or adversarial components (e.g., domain adversarial classifier), capsule layers, and/or other prediction models.

During backpropagation, the network learns a mapping function of weights by having the input feature vectors repeatedly presented in the training set and adjust the weights until a minimal error for all training sample sets is achieved. Error correlations are determined from the differences between the output and the expected output. Weights are adjusted in order to decrease the error. Thus, by mapping the input feature set to blood pressure values of the corresponding data set, prediction model 424 is trained through successive iterations of forward passes and backpropagation. During training, weights are initially randomized along with biases for each of the layers of the neural network. By forward passing and backpropagating the input feature vectors through the layers of the neural network, an error for the weighted coefficients can be determined. By adjusting the coefficients and iteratively repeating the forward pass and backpropagations, the error can be reduced to a negligible level of error.

In some embodiments, training prediction model 424 includes utilizing demographic information corresponding to the training data to classify each training data set based on the subject's demographic information. Demographic information may include the physical characteristics of the subject, relevant medical history, and other subject demographic data (e.g., age, body mass index, gender, height, weight, previous blood pressure samples, and previous medical conditions including cardiovascular diseases).

In some embodiments, in an offline training stage, external resources 426 may provide historical user templates as training data. In some embodiments, a subject may input as training data a historical user template containing PPG signals, demographic data, and blood pressure values that have been verified by an external source. Verifying blood pressure values can be performed by a healthcare provider at a doctor's office. For example, wearable device 102 may record a training PPG data set, which is recorded while a subject is in a doctor's office. To verify the PPG data, the subject concurrently performs an external blood pressure reading with a blood pressure cuff. The blood pressure cuff readings along with PPG signal data can be transmitted to external resources 426, via the Internet, as a PPG template for the subject. In the offline training mode, prediction model 424 is configured to retrieve the PPG template for the subject and train prediction model 424 with the PPG signal as input and the verified blood pressure values as output.

Once trained, prediction model 424 does not further utilize training data in making blood pressure predictions. In addition, prediction model 424 does not need actual blood pressure measurements to predict and/or otherwise determine blood pressure dip. As described above, system 100 (FIG. 1A) predicts and/or determines blood pressure dip based on PPG and motion sensor information. In an operational mode, prediction model 424, via processing component 306, receives features sets corresponding to PPG signal data of subject(s) 101. The trained prediction model 424 then outputs a prediction of the blood pressure level for each PPG window output by localization component 111.

Referring back now to FIG. 3, in some embodiments, BP determination component 324 is configured to input into the trained prediction model 424, the information determined from the PPG and motion sensors (e.g., the HRV features, the motion features, the awake or asleep classifications, etc.) worn by a subject (e.g., a subject 101 shown in FIG. 1), demographic information of the subject, historical blood pressure of the subject, PPG morphology templates, and/or other personal data of a subject. In some embodiments, demographic information of the subject may include, but is not limited to, age, body mass index, gender, height, weight, previous blood pressure samples, medical conditions including previous cardiovascular diseases, and other demographic information of the subject. Demographic information of the subject can be used to further increase the accuracy of the blood pressure predictions made by trained prediction model 424.

In some embodiments, blood pressure dip determination is performed by causing prediction model 424 to store each blood pressure prediction for every 30 second epoch of PPG signal data, along with awake/asleep conditions determined by physical state component 322. Responsive to aggregating a full 24 hour period of blood pressure predictions for individual PPG signal epochs, in some embodiments, prediction model 424 is caused to split the data into two categories. In some embodiments, the first category refers to diurnal blood pressure predictions, while the second category refers to nocturnal blood pressure predictions, as shown in FIG. 2. In some embodiments, prediction model 430 is caused to determine the average blood diurnal and nocturnal blood pressure as discussed above in FIG. 2, and determine a blood pressure dip based on the difference of the diurnal and nocturnal blood pressure divided by the average diurnal blood pressure, similar to the discussion above in FIG. 2. For each given day, the blood pressure dip is then output by processing component 306. In some embodiments, the blood pressure dip is categorized as either dipping, non-dipping, extreme dipping, or reverse dipping, as discussed above. Accordingly, having determined the blood pressure dip, processing component 306 is configured to cause transmission of the blood pressure dip to wearable device 108.

In some embodiments, BP determination component 324 is configured to determine an absolute blood pressure. Determining an absolute blood pressure level includes receiving a calibrated blood pressure reading of the subject. In some embodiments, because the PPG signal provides a relative blood pressure and not absolute, BP determination component 324 is configured to receive an external blood pressure reading to use as a reference in order to calibrate the relative blood pressure into an absolute blood pressure.

In some embodiments, receiving a calibration signal includes the subject performing a blood pressure reading with a standard cuff device. In some embodiments, the subject may have blood pressure readings performed with a standard cuff device at an external healthcare provider. The healthcare provider may then provide the blood pressure readings to system 300, via external resources 326 for example. In some embodiments, having performed a blood pressure reading with a cuff device, the subject may input the calibrated blood pressure reading via user interface 108. Having received the calibrated blood pressure reading, BP determination component 324 may output an absolute blood pressure value in mmHg, rather than a relative blood pressure in mmHg with an unknown offset. The relative blood pressure includes a zero point that is close to the subjects mean blood pressure. Therefore, analyzing the calibrated signal, the offset can be determined. Thus, with a single calibration signal, the offset for the entire 24 hour recording can be determined.

In some embodiments, external resources 326 include sources of information (e.g., databases, websites, etc.), external entities participating with system 300 (e.g., healthcare providers facilitating user PPG morphology templates, absolute blood pressure calibration information, demographic data, etc.), and/or other resources. For example, external resources 326 may include sources of PPG morphology training data for training the models, and/or other information. PPG morphology training data may be related to a subjects medical history and include various other historical, demographic, and medical information related to cardiovascular health of the subject. In some embodiments, external resources 326 include components that facilitate communication of information, one or more servers outside of system 300, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 326 may be provided by resources included in system 300. External resources 326 may be configured to communicate with processing component 306, wearable device 302, electronic storage 328, and/or other components of system 300 via wired and/or wireless connections, via a network (e.g., a local area network and/or the internet), via cellular technology, via Wi-Fi technology, and/or via other resources.

In some embodiments, electronic storage 328 comprises electronic storage media that electronically stores information. The electronic storage media of electronic storage 328 may comprise one or both of system storage that is provided integrally (i.e., substantially non-removable) with system 300 and/or removable storage that is removably connectable to system 300 via, for example, a port (e.g., a USB port, a firewire port, etc.) or a drive (e.g., a disk drive, etc.). Electronic storage 328 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 328 may store software algorithms, information determined by processing component 306, information received via wearable device 302 and/or external computing systems (e.g., external resources 326), and/or other information that enables system 300 to function as described herein. Electronic storage 328 may be (in whole or in part) a separate component within system 300, or electronic storage 328 may be provided (in whole or in part) integrally with one or more other components of system 300 (e.g., processing component 306).

Referring now to FIG. 5, FIG. 5 illustrates a method 500 for non-invasively determining blood pressure dip. The system comprises one or more processors and/or other components. The one or more processors are configured by machine readable instructions to execute computer program components. The computer program components include a windowing component, a localization component, an IBI component, an HRV feature component, a morphology feature component, a feature transformation component, a physical state component, and a blood pressure determination component. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 is implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/ or software to be specifically designed for execution of one or more of the operations of method 500.

In some embodiments, the method my begin at an operation 502, by receiving output PPG signals from the PPG sensor over a period of time and receiving output motion signals from the accelerometer over the period of time. In some embodiments, operation 502 is performed by a processing component the same as or similar to windowing component 311, of FIG. 3.

At an operation 504 determining, based on at least the PPG signals, one or more bloodflow features, the one or more bloodflow features indicating a variability of the bloodflow and/or a shape of a bloodflow curve over the period of time. In some embodiments, operation 504 is performed by a processing component the same as or similar to HRV feature component 316 and/or morphology feature component 318, of FIG. 3.

At an operation 506, the method includes determining, based on the motion signals, a physical state of the subject, the physical state indicating whether the subject is awake or asleep. In some embodiments, operation 506 is performed by a processing component the same as or similar to physical state component 322, of FIG. 3.

At an operation 508, the method includes providing the one or more bloodflow features and the physical state to a prediction model and causing the prediction model to determine the blood pressure dip of the subject for the period of time based on at least the one or more bloodflow features and the physical state. In some embodiments, operation 508 is performed by a processing component the same as or similar to blood pressure determination component 324, of FIG. 3.

At an operation 510, the method may conclude by causing transmission of the blood pressure dip to the wearable device. In some embodiments, operation 510 is performed by a processing component the same as or similar to blood pressure determination component 324, of FIG. 3.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for determining blood pressure dip in a subject via machine learning models, the system comprising:

a wearable device configured to be worn by the subject, the wearable device comprising:
    a photoplethysmographic (PPG) sensor configured to generate output signals conveying information related to a bloodflow of the subject; and
    a motion sensor configured to generate output signals conveying information related to motion of the subject; and
one or more processors operatively coupled to the wearable device and configured by machine-readable instructions to:
    receive output PPG signals from the PPG sensor over a period of time;
    receive output motion signals from the motion sensor over the period of time;
    determine, based on the motion signals, a motion level of the subject for a portion of the motion signals corresponding in time to a portion of the PPG signals;
    responsive to the motion level being less than a predetermined motion level, determine, based on the portion of the PPG signals, one or more bloodflow features indicating a variability of the bloodflow and/or a shape of a bloodflow curve over a period of time;
    determine, based on the PPG signals, a heart rate variability (HRV) of the subject over the period of time;
    determine, based on the HRV, a plurality of HRV features, the HRV features indicating changing characteristics of the heart rate variability over the period of time;
    determine an entropy gradient of the subject utilizing the plurality of HRV features and the motion signals in an ongoing manner over the period of time;
    determine, based on the entropy gradient, a physical state of the subject, the physical state being an awake state when it is determined that the entropy gradient is decreasing, and the physical state being an asleep state when it is determined that the entropy gradient is increasing;
    provide the one or more bloodflow features and the physical state to a machine learning model;
    cause the machine learning model to determine the blood pressure dip of the subject for the period of time based on the one or more bloodflow features and the physical state; and
    cause transmission of the blood pressure dip to the wearable device.

2. The system of claim 1, wherein the one or more processors are configured such that determining the one or more bloodflow features of the subject further comprises:
    determining, based on the PPG signals, a plurality of PPG morphology features, the morphology features indicating changing characteristics of the shape of the bloodflow curve over the period of time;
    determining, utilizing the machine learning model, a blood pressure over the period of time based on the plurality of HRV features and/or the plurality of PPG morphology features; and
    determining the blood pressure dip based on the blood pressure over time.

3. The system of claim 1, wherein the one or more processors are configured such that determining the one or more bloodflow features of the subject comprises:
    determining a PPG morphology of a portion of the PPG signals;
    determining an anticipated shape of the portion of the PPG signals; and
    determining, utilizing the portion of the PPG signals, the one or more bloodflow features of the subject responsive to the PPG morphology corresponding to the anticipated shape of the PPG morphology.

4. The system of claim 3, wherein the one or more processors are configured such that determining the one or more bloodflow features of the subject comprises:
    determining a motion level of the subject corresponding in time to a portion of the PPG signals; and
    determining, utilizing the portion of the PPG signals, the one or more bloodflow features of the subject responsive to the motion level corresponding to less than a predetermined motion level.

5. The system of claim 4, wherein determining the physical state includes extracting a plurality of motion features from the motion signal, and wherein the plurality of HRV features, the plurality of morphology features, and the plurality of motion features are, at least partially, extracted utilizing one or more machine learning models.

6. The system of claim 1, wherein the wearable device comprises a smart watch.

* * * * *